(12) United States Patent
Desaute et al.

(10) Patent No.: US 10,598,813 B2
(45) Date of Patent: Mar. 24, 2020

(54) EQUIPMENT FOR THE RADIOGRAPHY OF A LOAD, COMPRISING A REFERENCE BLOCK, AND ASSOCIATED METHOD

(71) Applicant: SMITHS HEIMANN SAS, Vitry sur Seine (FR)

(72) Inventors: Pascal Desaute, Paris (FR); Irène Dorion, Paris (FR); Nicolas Dumay, Dampierre en Yvelines (FR)

(73) Assignee: SMITHS HEIMANN SAS, Vitry sur Seine (FR)

( * ) Notice: Subject to any disclaimer, the term of this patent is extended or adjusted under 35 U.S.C. 154(b) by 805 days.

(21) Appl. No.: 14/362,687

(22) PCT Filed: Dec. 5, 2012

(86) PCT No.: PCT/EP2012/074543
§ 371 (c)(1),
(2) Date: Jun. 4, 2014

(87) PCT Pub. No.: WO2013/083648
PCT Pub. Date: Jun. 13, 2013

(65) Prior Publication Data
US 2014/0341342 A1   Nov. 20, 2014

(30) Foreign Application Priority Data

Dec. 5, 2011   (FR) ..................................... 11 61152

(51) Int. Cl.
*G01V 5/00*   (2006.01)
*G01T 1/29*   (2006.01)
(Continued)

(52) U.S. Cl.
CPC ......... *G01V 5/0066* (2013.01); *G01N 23/083* (2013.01); *G01N 23/10* (2013.01);
(Continued)

(58) Field of Classification Search
CPC .. H05G 1/00; H05G 1/02; H05G 1/08; H05G 1/26; H05G 1/60; H05G 1/64;
(Continued)

(56) References Cited

U.S. PATENT DOCUMENTS

| 4,472,823 A | 9/1984 | Waltham |
| 4,907,157 A | 3/1990 | Uyama |

(Continued)

FOREIGN PATENT DOCUMENTS

| EP | 2293049 A2 | 3/2011 |
| JP | 63181740 A | 7/1988 |

OTHER PUBLICATIONS

International Search Report and Opinion dated Feb. 13, 2013 in PCT Application No. PCT/EP2012/074543.

*Primary Examiner* — Anastasia Midkiff
(74) *Attorney, Agent, or Firm* — Eric L. Lane; Green Patent Law

(57) ABSTRACT

The invention relates to equipment (1) for the radiography of a load (11) moving relative thereto, the radiography equipment comprising a source (2) for emitting pulses (16) of divergent X-rays, a collimator (4) for the source for delimiting an incident x-ray beam (22), and sensors (8) for receiving X-rays, which are aligned with the incident beam so as to collect the X-rays after the latter have passed through the load and generate raw image signals. The equipment includes a reference block (6) comprising intermediate x-ray sensors (28) which are to be located within the incident beam, between the source and the load, so as to be irradiated by at least two separate angular sectors of the incident beam, and which are to output separate reference signals corresponding to each angular sector to be used in the conversion of raw image signals into a portion of a radiographic image. The invention also relates to a corresponding method.

16 Claims, 4 Drawing Sheets

(51) Int. Cl.
*G01N 23/10* (2018.01)
*G01T 1/16* (2006.01)
*G01N 23/083* (2018.01)
*G01T 1/02* (2006.01)
*G01N 23/04* (2018.01)

(52) U.S. Cl.
CPC ............ G01T 1/026 (2013.01); G01T 1/1603 (2013.01); G01T 1/2907 (2013.01); G01T 1/2978 (2013.01); G01V 5/0016 (2013.01); *G01N 23/04* (2013.01); *G01N 2223/04* (2013.01); *G01N 2223/3307* (2013.01); *G01N 2223/3308* (2013.01); *G01N 2223/503* (2013.01)

(58) Field of Classification Search
CPC ........ G01N 23/00; G01N 23/02; G01N 23/04; G01N 23/06; G01N 23/08; G01N 23/083; G01N 23/087; G01N 23/10; G01N 2223/00; G01N 2223/03; G01N 2223/04; G01N 2223/10; G01N 2223/101; G01N 2223/1016; G01N 2223/30; G01N 2223/304; G01N 2223/33; G01N 2223/3307; G01N 2223/3308; G01N 2223/40; G01N 2223/401; G01N 2223/41; G01N 2223/413; G01N 2223/419; G01N 2223/42; G01N 2223/50; G01N 2223/503; G01N 2223/63; G01N 2223/639; G01T 1/00; G01T 1/02; G01T 1/023; G01T 1/026; G01T 1/16; G01T 1/1603; G01T 1/1606; G01T 1/20; G01T 1/2006; G01T 1/2018; G01T 1/24; G01T 1/243; G01T 1/29; G01T 1/2907; G01T 1/2914; G01T 1/2964; G01T 1/2971; G01T 1/2978; G01T 1/2985; G01V 5/00; G01V 5/0008; G01V 5/0016; G01V 5/005; G01V 5/0066
See application file for complete search history.

(56) References Cited

U.S. PATENT DOCUMENTS

| | | | | |
|---|---|---|---|---|
| 5,493,596 A | * | 2/1996 | Annis | G01N 23/10 378/146 |
| 6,118,850 A | * | 9/2000 | Mayo | G01N 23/2076 378/82 |
| 2011/0274249 A1 | * | 11/2011 | Gray | G01V 5/0025 378/87 |

* cited by examiner

EQUIPMENT FOR THE RADIOGRAPHY OF A LOAD, COMPRISING A REFERENCE BLOCK, AND ASSOCIATED METHOD

BACKGROUND OF THE INVENTION

Field of the Invention

The present invention relates to equipment for the radiography of a load, the equipment and the load being designed to move relative to one another during the detection, the radiography equipment comprising:
- a source for emitting pulses of divergent X-rays;
- a collimator for the source for delimiting an incident x-ray beam designed to irradiate a section of the load, the successive x-ray pulses being capable of irradiating successive sections of the load; and
- sensors for receiving X-rays situated in the extension of the incident beam to receive the X-rays after they have passed through the load and generate raw image signals designed to be converted into a radiographic image portion corresponding to said section.

Description of Related Art

In order to detect the presence of suspicious objects such as contraband, weapons or explosive devices, it is known to use x-ray radiography equipment to develop an image by transmission of the content of the load. Such devices are for example used in airports, in order to inspect passengers' luggage. They are also used at various checkpoints, in particular at customs to monitor the content of containers or truck trailers.

In general, this radiography equipment provides a gray-scale or color image of the content of the loads. The recognition of the objects contained in the load is done by an operator who looks at the images provided by the equipment. It will be understood that effective detection requires a high-quality and relevant image.

More specifically, in known equipment, the source emits x-ray pulses at a frequency of approximately 200 Hz to irradiate the successive sections of the load. The radiation transmitted by the load passes through the receiving sensors situated in the extension of the incident beam. The sensors measure a received x-ray dose. In general, the radiographic sections are vertical and the signals transmitted by the receiving sensors are converted into pixel values to form a column of the image shown to the operator.

In the source, the X-rays are obtained by orienting an electron flow accelerated at a given energy, typically several MeV, on a metal target. The deceleration of the electrons in the target causes the emission of x-ray photons, the energy of which is comprised between 0 and several MeV. The emission is primarily done in the axis of the electron beam, but also in all angular directions around that axis.

However, due to certain instabilities of radiography equipment, successive sections of the same load are not irradiated in the same way. On the one hand, the x-ray sources used are not stable over time. They experience an evolution in the intensity of the beam during detection. There are also instabilities from one pulse to the next, affecting the intensity of the pulses as well as the spectral properties of the incident beam. On the other hand, the equipment may be affected by mechanical instabilities regarding the relative position of the sensors and the x-ray source.

These instabilities cause a deterioration of the obtained radiographic image, for example vertical streaks or uneven intensities from one line to the next.

To offset this problem, radiography equipment of the state of the art comprises a reference block including an intermediate x-ray sensor situated in the incident beam, between the source and the load to the radiographed. This sensor is placed separated from the target and, seen from the source, occupies the smallest possible solid angle in order to minimize the disruption of the incident beam. Its role is to record a received x-ray dose, at the same time as the receiving sensors. It is thus possible to correct the doses received by the receiving sensors based on the dose received by the sensor of the reference block.

However, it has been observed that such a correction is not always sufficient, and that the quality of the obtained radiographs is not always suitable to allow adequate detection.

This is in particular the case if one wishes to obtain information on the chemical nature of the material passed through by the X-rays. Such detection may be done by successively lighting each section of the load using x-ray pulses obtained by applying different electron acceleration voltages and comparing the obtained images to predefined values. This may, however, prove difficult and imprecise in practice, in particular in light of the aforementioned instabilities.

One aim of the invention is to provide equipment for the radiography of a load, providing images with improved quality, making it possible, if applicable, to obtain information on the chemical nature of the materials passed through.

BRIEF SUMMARY OF THE INVENTION

To that end, the invention relates to radiography equipment of the aforementioned type, further including a reference block including intermediate x-ray sensors which are to be located each, at least partially, in the incident beam, between the source and the load, the intermediate sensors being designed to be irradiated by at least two separate angular sectors of the incident beam and to provide independent reference signals corresponding to each angular sector to be used in the conversion of the raw image signals into a portion of the radiographic image.

"Separate" angular sectors of the incident beam means that the angular directions comprised in those angular sectors pass through the intermediate sensors of the corresponding reference block, advantageously at angles separated by at least 1°, preferably by at least 5°, and still more preferably at least 20° in the median plane.

According to specific embodiments, the radiography equipment may comprise one or more of the following features, considered alone or according to any technically possible combination(s):
- the incident beam having a given angular opening in a median plane, the reference block comprises a plurality of intermediate sensors occupying, in the median plane, an angular opening corresponding to at least 50% of said given angular opening, preferably at least 90%;
- the intermediate sensors are substantially aligned, preferably regularly, in a direction R of the median plane;
- the direction R is substantially perpendicular to a main direction L of the incident beam in which the intensity of the incident beam is maximal;
- the radiography equipment includes a control and signal processing device capable of creating each radiographic portion by correcting each raw image signal collected in a given angular sector of the beam based on a reference signal obtained for the same given angular sector from the reference signals generated by the intermediate sensors for the same x-ray pulse;

the intermediate sensors assume the form of bars;

the intermediate sensors all have the same working detection volume;

each receiving sensor is capable of receiving an individual angular sector of the incident beam after the successive passage of the incident beam in the reference block, then in the intermediate space optionally occupied by the load to be radiographed;

the incident beam is collimated so that the receiving sensors occupy the entire extension of the incident beam perpendicular to a median plane of the incident beam.

The invention also relates to a method for the radiography of a load in order to perform detection, the method comprising the following steps:

a) emitting a pulse of divergent X-rays from a source, the load and the source being in motion relative to one another;

b) from the x-ray pulse, forming an incident x-ray beam using a collimator, and irradiating a section of the load extending along a median plane; and c) collecting the X-rays after they pass through the load in receiving sensors situated behind the load in the extension of the incident beam, and generating raw image signals corresponding to the x-ray doses received by the receiving sensors;

steps a) and b) being iterated on successive sections of the load so as to obtain a radiographic image of the load;

the method further comprising a step d) in which a measurement is done of the x-ray doses received by at least two intermediate sensors of a reference block situated in the incident beam so as to be passed through by at least two separate angular sectors of the incident beam delimited in step b), generating independent reference signals corresponding to the doses measured by the intermediate sensors in each angular sector, and correcting the raw image signals obtained in step c) using reference signals.

According to specific embodiments, the radiography method may comprise one or more of the following features, considered alone or according to any technically possible combinations(s):

in step d), the incident beam delimited in step b) having a given angular opening in the median plane, x-ray doses received by a plurality of intermediate sensors of the reference block situated in the incident beam so as to occupy an angular opening corresponding to at least 50% of said given annular opening, preferably at least 90%, are measured;

in step d), each raw image signal generated in step c) is corrected using a receiving sensor in a given angular sector of the beam through a calculation using a reference signal obtained for the same given angular sector from the reference signals generated by the intermediate sensors;

in step d), the reference signals created by the intermediate sensors are resampled in order to obtain the reference signals angularly corresponding with the raw image signals;

in step d), an intrinsic energy of the incident beam is evaluated from the reference signals and the raw image signals obtained in step c) are corrected through a calculation using said intrinsic energy;

the evaluation of the intrinsic energy includes the following phases:

a measured angular distribution of the reference signals obtained for a given x-ray pulse from measured reference signals is established;

the measured angular distribution is compared with predetermined angular distributions corresponding to different intrinsic energies; and the measured angular distribution is associated with a predetermined angular distribution, and the intrinsic energy of the predetermined angular distribution is assigned to the given x-ray pulse;

in step d), an intrinsic gain energy of the reference block is further determined and said intrinsic energy of the reference block is taken into account in correcting the raw image signals obtained in step c);

in step a), a first x-ray pulse is emitted at a first intrinsic reference energy, and a second x-ray pulse is next emitted at a second intrinsic reference energy separate from the first intrinsic reference energy, the method comprising the following steps:

determining the intrinsic energy corresponding to each x-ray pulse;

correcting the raw image signals respectively corresponding to each x-ray pulse using the intrinsic energy respectively determined for each x-ray pulse; and reconstituting a unique image from the corrected image signals, said unique image having information representative of the average atomic numbers of materials of the load;

the unique image is reconstituted, for each pixel, from the corrected image signals of said pixel and a conversion table depending on the intrinsic energies of the first and second x-ray pulses having generated the raw images of said pixel.

BRIEF DESCRIPTION OF THE SEVERAL VIEWS OF THE DRAWING(S)

The invention will be better understood upon reading the following description, provided solely as an example and done in reference to the appended drawings, in which.

DETAILED DESCRIPTION OF THE INVENTION

Figure 1:
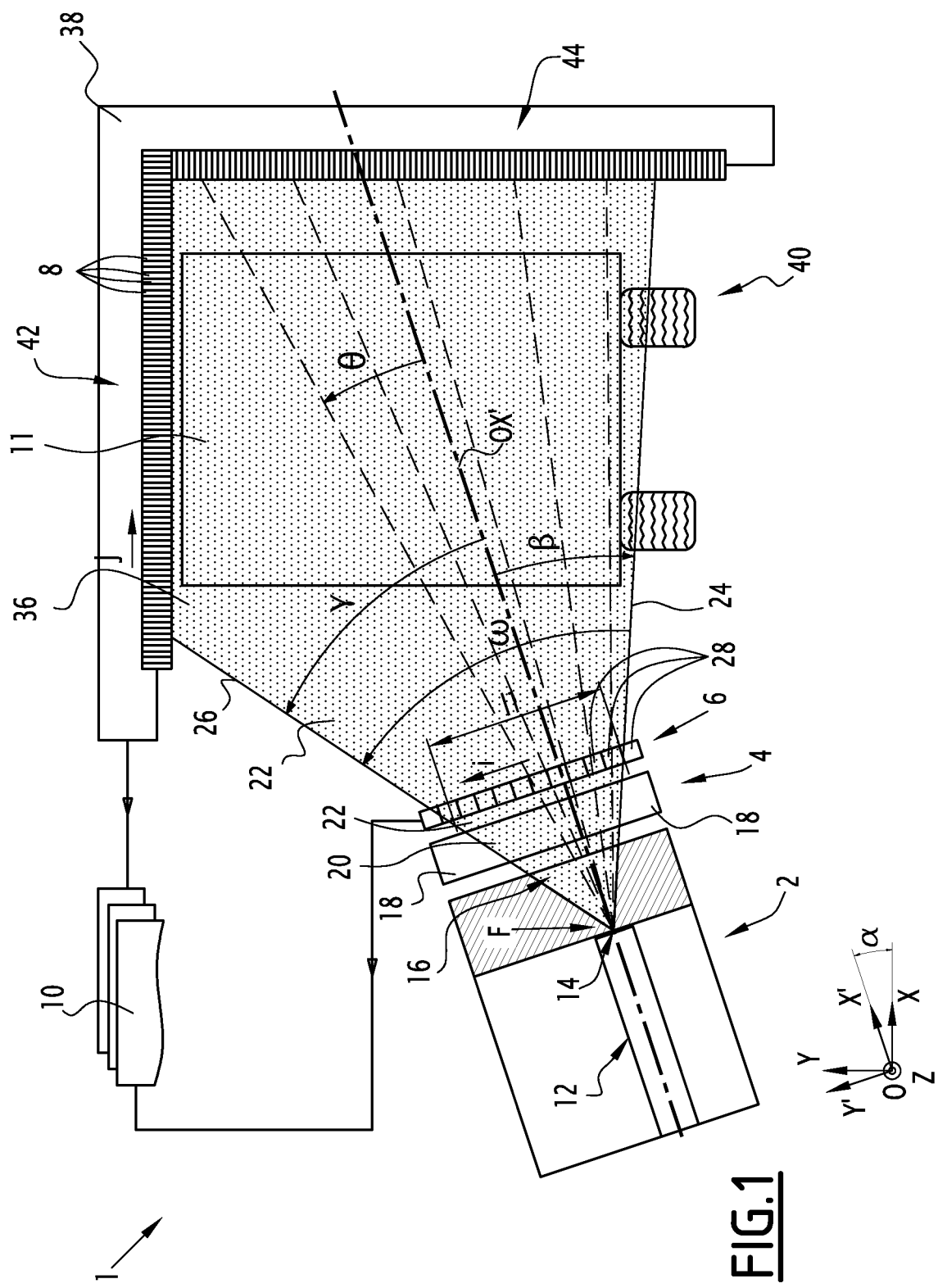
FIG. 1 shows radiography equipment according to the invention in side and sectional view.

FIG. 1 shows a radiography equipment 1 according to the invention. The equipment 1 will be described in reference to an orthonormal reference OXYZ, axis OY being the ascending vertical, plane XOY being vertical, plane XOZ being horizontal.

The equipment comprises an x-ray source 2, a collimator 4, a reference block 6, receiving sensors 8 and a control and signal processing device 10. It is designed for the radiography of a load 11.

The x-ray source 2 comprises a device for producing and accelerating an electron beam 12. It further comprises a target 14 for the electron beam comprising a metal such as tungsten and copper so as to generate a divergent x-ray pulse 16 from a focal point F.

The photons of the x-ray pulse 16 are for example generated by the so-called braking radiation effect, or Bremsstrahlung. The energy of the photons is comprised between 0 and a maximum value E that will be designated hereinafter using the expression "intrinsic energy" or "intrinsic energy parameter". This intrinsic energy E corresponds to the complete transformation of the kinetic energy of the accelerated electrons into radiating energy. The electrons are generally accelerated under a voltage comprised between 1 MV and 10 MV, thus the intrinsic energy of the beam is comprised between 1 MeV and 10 MeV.

In a first alternative, the x-ray source 2 emits successive x-ray pulses 16 having substantially the same intrinsic energy E, generally comprised between 1 MeV and 10 MeV, for example approximately 4 MeV. The pulses 16 are emitted at a given frequency, comprised between 50 Hz and 1000 Hz, for example approximately 200 Hz.

In a second alternative, the x-ray source 2 alternatively emits x-ray pulses 16 with a high intrinsic energy E1, for example greater than or equal to approximately 6 MeV, then with a low intrinsic energy E2, for example less than or equal to approximately 4 MeV. This mode is called "interlaced". The pulses are emitted at a given frequency, for example approximately 400 Hz.

The intensity of the x-ray pulses 16 is maximal in a direction OX', called "main direction", belonging to the plane XOY, situated in the extension of the accelerated electron beam. In the example illustrated in FIG. 1, the direction OX' forms a positive angle $\alpha$ with the axis OX, comprised between 10° and 20°, for example approximately 13°. A direction OY' perpendicular to the direction OX' is further defined, the reference OX'Y'Z being orthonormal.

The collimator 4 extends at the output of the x-ray source 2 substantially in direction OY'. It includes a wall 18 substantially opaque to X-rays delimiting a slot 20 oriented in plane XOY in direction OY'. Thus, the collimator 4 is capable of generating an incident x-ray beam 22 essentially comprised in plane XOY, which is a median plane for the incident beam.

Advantageously, the slot 20 has a length l1 in direction OY' comprised between 20 cm and 100 cm, and it is with between 0.5 mm and 10 mm.

The thickness e of the incident beam created at the output of the collimator 4 along the axis Z is substantially equal to the width 12 of the slot.

In the median plane XOY, the incident beam 22 has an angular opening $\omega$ extending from a lower direction 24 forming an angle $\beta$ with the main axis OX' to an upper direction 26 forming an angle $\gamma$ with the axis OX'. The opening $\omega$ measured from the focal point F in plane XOY is for example comprised between 30° and 70°, and in particular approximately 50°.

The x-ray source 2 and the collimator 4 are positioned at a distance of several meters from the load 11, such that the incident beam 22 makes it possible to irradiate the entire load 11 in the median plane XOY.

The reference block 6 is designed to be inserted between the collimator 4 and the load 11 to be passed through by at least part of the incident beam 22.

The reference block 6 extends substantially in direction OY', i.e., it is substantially perpendicular to the main direction OX' of the incident beam 22. More specifically, in this example, the reference block 6 is placed across from the slot 20 of the collimator 4 so as to be passed through by the entire angular expanse co of the incident beam 22.

The reference block 6 comprises a plurality of intermediate x-ray sensors 28.

The intermediate sensors 28 of the reference block 6 and the receiving sensors 8 are numbered and individually electrically connected to the control and signal processing device 10.

Each intermediate sensor 28 includes a scintillator 30 mounted on a printed circuit 32.

The printed circuit 32 of each intermediate sensor 28 comprises a photodiode and an electric capacitor (not shown).

Figure 2:
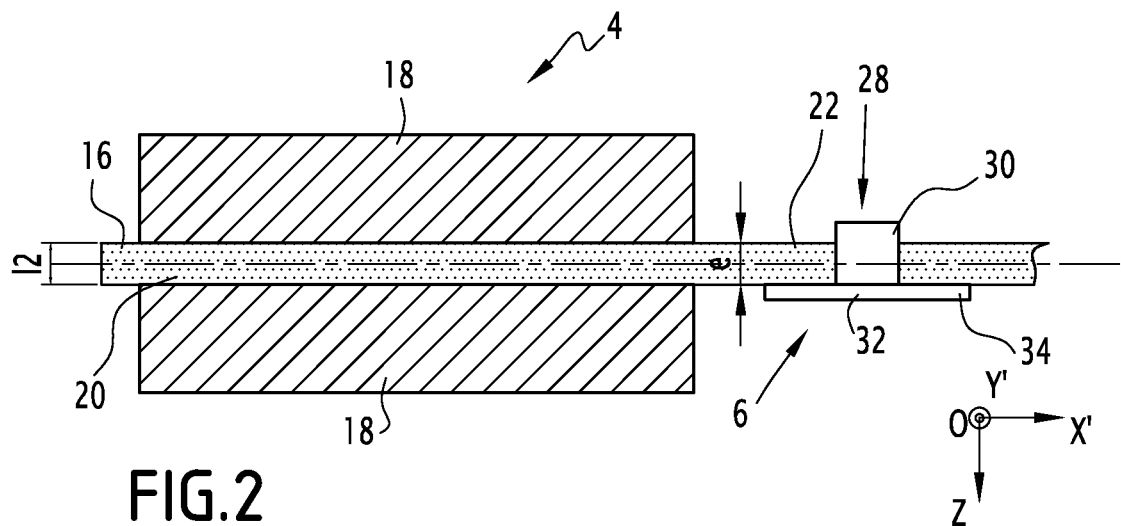
FIG. 2 is a top view of the x-ray source and the reference block of the radiography equipment shown in FIG. 1.

According to one particular embodiment illustrated in FIG. 2, the reference block 6 is configured so that the scintillators 30 are situated substantially in the incident beam 22 and the photodiodes are situated substantially outside the incident beam. This makes it possible to increase the lifetime of the photodiodes. In particular, the scintillators 30 are placed across from the slot 20 of the collimator 6 in plane XOY and the printed circuits 32 are positioned while being laterally offset in direction OZ relative to the slot 20.

Each printed circuit 32 is coupled to the control and signal processing device 10.

The intermediate sensors 28 are positioned adjacent to one another along a sensor row extending across from the slot 20 of the collimator 6. The adjacent intermediate sensors 28 thus extend angularly over an angle A corresponding to more than 50°, in particular more than 90° of the opening angle $\omega$ of the beam 22 created by the collimator 6.

The angle A is defined between the source and the two sensors 28 situated at the ends of the row of sensors 28 on the reference block 6.

In the example illustrated in FIG. 2, the intermediate sensors 28 extend linearly along an axis parallel to direction OY', therefore parallel to the slot 20. They thus form a sensor bar with height h in direction OY'.

According to one particular embodiment, the reference block 6 comprises a number N1 of intermediate sensors 28 comprised between 100 and 500, in particular 160.

The distance along the axis OX' separating the slot 20 from the reference block 6 is advantageously comprised between 1 and 2 cm.

Figure 3:
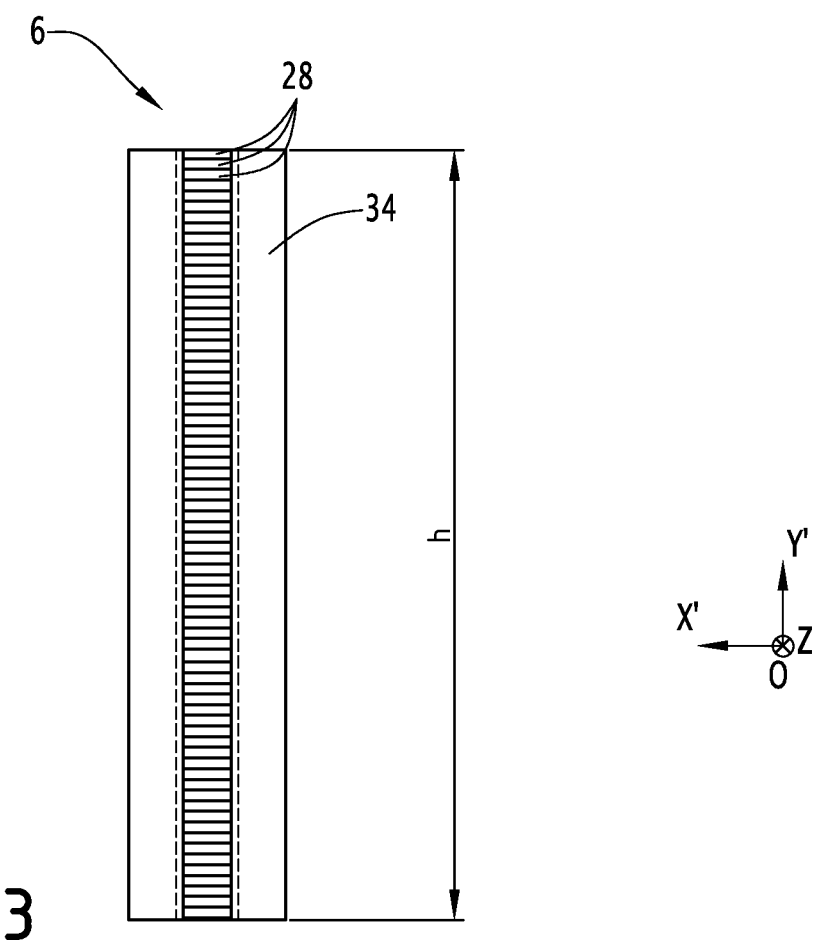
FIG. 3 shows the reference block illustrated in FIG. 2 in side view.

According to one particular embodiment illustrated in FIG. 3, each printed circuit 32 is located on a vertical wafer 34. The wafer is advantageously approximately 7 mm wide in direction OX' and approximately 1 m long in direction OY'.

In particular, the scintillators 30 are regularly spaced apart in direction OY'. They for example have a section of 4 mm×4 mm in plain X'OZ. Advantageously, the scintillators 30 for example have a base of cesium iodide (CsI), cadmium tungstate ($CdWO_4$) or gadolinium oxysulfide (GOS: $Gd_2O_2S$).

Each photodiode is capable of receiving the photons emitted by one of the scintillators 30 and emitting a current.

The photodiode is further electrically connected to a capacitor, which in turn is connected to the control and signal processing device 10.

Each intermediate sensor 28 is thus capable of being irradiated by an individual angular sector of the incident beam 22 and of creating a reference signal $I_{BR}$ that is representative of the intensity of the incident beam 22 in the individual angular sector in question.

The angular expanse of each angular sector of the incident beam received by an intermediate sensor 28 is for example less than 5°, and is in particular comprised between 0.2° and 0.4°. This individual angular expanse can vary along the intermediate sensor bar 28, in particular when the intermediate sensors 28 are aligned along a straight line.

The printed circuit 32 of each intermediate sensor 28 is individually connected to the control and signal processing device 10 to allow the latter to receive a reference signal $I_{BR}$ coming from each intermediate sensor 28, in order to correct the image, as will be described below.

The receiving sensors 8 are positioned in the extension of the incident beam 22. They delimit, with the reference block 6, an intermediate space 36 for the passage of the load 11 to be radiographed.

According to one particular embodiment, the number N2 of receiving sensors 8 is greater than the number N1 of intermediate sensors 28. N2 is for example greater than 1000, in particular equal to 1200.

Each intermediate sensor 28 is advantageously situated on a straight line connecting a receiving sensor 8 to the focal point F of the x-ray source 2.

The receiving sensors 8 are adjacent to one another. They extend along a broken line situated substantially in median plane XOY.

According to one embodiment, the receiving sensors 8 are mounted on a gantry 38. The gantry 38 for example forms an inverted "L" extending in a median plane XOY. The load 11, for example carried by a vehicle 40, is designed to pass into the intermediate space 36 below that gantry 38.

The receiving sensors 8 of a first assembly 42 extend in direction OX and form the base of the inverted "L". The receiving sensors 8 of the first assembly 42 are situated above the intermediate space 36.

The receiving sensors 8 of a second assembly 44 extend in the vertical direction OY and form the shaft of the inverted "L".

Each receiving sensor 8 has a structure similar to that of an intermediate sensor 28. It comprises a scintillator and a printed circuit comprising a photodiode and a capacitor. Alternatively, it is possible to perform a direct detection, using a receiving sensor 8 made from a fixed semiconductor, of the CdTe type.

Each receiving sensor 8 is capable of receiving an individual angular sector of the beam 22 after it has successively passed through a reference block 6, then the intermediate space 36 optionally occupied by the load 11 to be radiographed.

Each receiving sensor 8 is capable of creating a raw image signal $I_{brut,L}$ that is representative of the intensity of the beam 22 in the considered individual angular sector, optionally after passage in the load 11 to be radiographed.

The printed circuit of each receiving sensor 8 is individually connected to the control and signal processing device 10 to allow the latter to receive the raw image signal $I_{brut,L}$ coming from each receiving sensor 8.

The control and signal processing device 10 is connected to the x-ray source 2 so as to be able to monitor it, to each receiving sensor 8, and to each intermediate sensor 28, in order to receive the signals $I_{brut,L}$ and $I_{BR}$ corresponding to the x-ray doses received by the sensors 8, 28.

The control and signal processing device 10 is capable of collecting and processing the received signals $I_{brut,L}$ and $I_{BR}$. The control and signal processing device 10 according to the invention includes means for correcting each raw image signal created by a receiving sensor 8 using the reference signal obtained in the same angular sector from an intermediate sensor 28 for the same pulse. This reference signal is for example created by an intermediate sensor 28 situated in the same angular sector, or is calculated from the signal created by at least one sensor 28 by interpolating or extrapolating the signal created by the sensor 28 in the angular sector of the receiving sensor 8.

The control and signal processing device 10 further includes means for forming an image based on each corrected image signal obtained from the angular correction means.

The load 11 is designed to be moved relative to the equipment 1 so that successive sections of the load 11 are radiographed.

In a first alternative, the load 11 is carried by a vehicle 40 capable of moving at a selected speed relative to the x-ray source 2 and the sensors 8, 28 so as to pass through the plane XOY.

According to one particular embodiment, the vehicle 40 is designed to pass through the plane XOY substantially perpendicularly.

Alternatively, the equipment 1 includes an assembly (not shown) for moving the load capable of performing the movement at a given speed.

The given movement speed is thus comprised between 0 m/s and 15 m/s. It can be increased if the frequency of the x-ray pulses 16 is increased.

Upon each x-ray pulse 16, a particular section of the load 11 is radiographed.

The implementation of a method for the radiography of a load 11 using the equipment 1 according to the invention will now be described in one particular example of a load 11 carried by a vehicle 40.

The vehicle 40 carrying the load 11 on which detection is desired passes under the gantry 38 containing the receiving sensors 8. The passage typically lasts between 10 seconds and 60 seconds, depending on the length of the load 11 and the speed of the vehicle 40. The x-ray source 2 is activated once the cab of the vehicle 40 has passed through the median plane XOY, so as not to irradiate the driver of the vehicle 40 if the driver is present in the cab. Alternatively, the x-ray source 2 can be activated before the cab of the vehicle 40 passes through the median plane XOY.

According to a first embodiment of the radiography, the x-ray source 2 emits x-ray pulses at a given frequency, for example 200 Hz.

In this first embodiment, the x-ray pulses 16 all have substantially the same intrinsic energy E, for example approximately 6 MeV. The operation of the x-ray source 2 is known in itself and will not be described in detail.

The collimator 4 forms an incident beam 22 that irradiates successive sections of the load 11 carried by the vehicle 40. Hereinafter, the successive sections are numbered using an index k.

Upon each x-ray pulse 16, an incident beam 22 with angular expanse w is created at the output of the collimator 4 at the slot 20. This beam has an intrinsic energy E substantially equal to a reference energy, for example 6 MeV.

Upon each x-ray pulse 16, each receiving sensor 8 and each intermediate sensor 28 measure a received x-ray dose in the space occupied by their respective scintillators 30. In other words, each receiving sensor 8 and each intermediate sensor 28 measure an intensity received in the angular sector of the beam 22 occupied by their respective scintillators 30.

In particular, the beam 22 passes through the reference block 6. Each intermediate sensor 28 is irradiated by an angular sector of the incident beam 22 and then creates a raw reference signal $I_{brut,BR}(i,k)$, where i is the number associated with the intermediate sensor 28, comprised between 1 and N1, and k is the number of the pulse, corresponding to a section of the load 11 when the latter is presented in the intermediate space 36.

The measuring method of the sensors 8, 28 is known in itself. The X-rays of the beam 22 deposit a certain dose in the scintillators 30, the dropout of which causes the emission of visible photons. The energy of the photons emitted by each scintillator 30 is converted into a current by each photodiode. Advantageously, the current is next integrated by the capacitor, which provides a voltage across its terminals representative of the received dose. The voltage of the capacitor constitutes the working signal transmitted to the control and signal processing device 10.

Then, after it passes through the reference block 6, the beam 22 passes through the intermediate space 36 and a section of the load 11, if the latter is present.

The beam 22 interacts with the material present in the intermediate space 36, in particular by x-ray absorption. After passage in the intermediate space 36, the beam 22 has a more or less attenuated intensity.

Next, the more or less attenuated beam 22 is collected by the receiving sensors 8. Each receiving sensor 8 is irradiated by an angular sector of the beam 22 and then creates a raw image signal $I_{brut,L}(j,k)$, where j is the number associated with the receiving sensor 8, comprised between 1 and N2, and k is the pulse number, corresponding to a section when the load 11 is present.

According to one embodiment, M x-ray pulses are sent, M being high enough to cover the load 11 and to have N "open flame" pulses, i.e., sent when the load 11 is not present in the intermediate space 36, for example after the load 11 has passed in the median plane XOY. The so-called "open flame" pulses serve as a reference for the gain, as will be seen below.

The control and signal processing device 10 therefore acquires, for each x-ray pulse k, reference signals $I_{brut,L}(i,k)$ coming from the intermediate sensors 28 of the reference block 6 and raw image signals $I_{brut,L}(j,k)$ coming from receiving sensors 8, with:

i, index of the intermediate sensor, going from 1 to N1, j, index of the receiving sensor, going from 1 to N2, k, pulse index, going from 1 to M, for detection with a duration typically comprised between 10 s and 60 s.

M is for example greater than 1000, in particular greater than 2000, and for example equal to 3000.

N is for example comprised between 100 and 300, for example equal to approximately 200.

After the usual validity tests of the signals $I_{brut,L}(j,k)$ and $I_{brut,BR}(i,k)$, those raw signals are corrected by the offsets using a method known in itself.

Then, an individual gain is calculated for each intermediate sensor 28 using the "open flame" pulses:

$$VGain_{BR}(i) = \frac{\sum_{k=M-N+1}^{M} I_{brut,BR}(i,k)}{N} \text{ with } i = 1 \text{ to } N1,$$

and for each receiving sensor 8:

$$VGain_{L}(j) = \frac{\sum_{k=M-N+1}^{M} I_{brut,L}(j,k)}{N} \text{ with } j = 1 \text{ to } N2.$$

A correction is thus done of the raw signal obtained by each sensor 8, 28 upon each pulse by the respective gains:

$$\begin{cases} I_{BR,1}(i,k) = \frac{I_{brut,BR}(i,k)}{VGain_{BR}(i)} \\ I_{L,1}(j,k) = \frac{I_{brut,L}(j,k)}{VGain_{L}(j)} \end{cases}$$

with $i = 1$ to $N1$, $j = 1$ to $N2$, $k = 1$ to $M$

If N1 is different from N2 as in the example, the reference signals are angularly resampled in order to have the same number of reference values as there are receiving sensors 8, with an angle correspondence:

$$I_{BR,2}(j,k) = \text{interp}(\theta_{BR}(i), I_{BR,1}(i,k), \theta_L(J)),$$

$\theta_{BR}$ and $\theta_L$ being the angles from which the intermediate sensor 28 with index i and the receiving sensor 8 with index j are seen, the function interp(x,y,xi) performing an interpolation of the function y(x) toward yi(xi). This interpolation may for example be linear.

For each index i corresponding to a receiving sensor 8, $I_{BR,2}(i,k)$ is therefore a reference signal obtained in the same angular sector as that of the receiving sensor 8. This reference signal corresponds to the dose received by a fictitious intermediate sensor, passed through by the same angular sector of the x-ray beam as the receiving sector 8 with index j.

Then, the image signals already corrected by the offsets and the gains are divided by the reference signals:

$$I_{corr,L}(j,k) = \frac{I_{L,1}(j,k)}{I_{BR,2}(j,k)},$$

the angular sector correspondence being respected.

The image is thus corrected of any angular disparities for a same pulse k and disparities between pulses.

According to a second embodiment, the intrinsic energy E(k) of each x-ray pulse 16 is determined based on reference signals $I_{BR}(i,k)$ created by the different intermediate sensors 28 for the pulse in question.

In particular, an angular distribution of the intensities of the beam 22 $I_{BR}(\theta,k)$ is determined using the individual values of the reference signals $I_{BR}(i,k)$ and associating each of them with a given angle $\theta$ corresponding to the mean angle of the intermediate sensor 28 with index i relative to the main direction OX'.

The angular distribution measured for each pulse k is normalized by its maximum value, after any filtration if the noise is high enough to disrupt the measurements. A normalized angular distribution $I_{BR}(\theta,k)^*$ is thus obtained.

The latter is compared to a normalized regular distribution database obtained by simulation for a range of intrinsic energies E. This simulation is done based on the known geometry of the equipment 1, for example using the GEANT software.

The intrinsic energy E(k) of each pulse k is then determined as being the intrinsic energy E associated with the normalized angular distribution of the database closest to the normalized angular distribution $I_{BR}(\theta,k)^*$.

The larger the angular coverage of the beam 22 by the reference block 6 is, the better the determination of the intrinsic energy E of the x-ray pulses 16 is.

An intrinsic gain energy $E_L$ is also determined based on an "open flame" pulse, for example based on the gain vector of the reference block 6, $VGain_{BR}(i)$, with i=1 to N1. This can be done in the manner described above to determine the intrinsic energy E(k) of each pulse k. The intrinsic gain energy $E_L$ representative of the angular distribution of the profile $VGain_{BR}(i)$ is obtained.

A finite correction $I_{corr,L2}(j,k) = I_{corr,L}(j,k) \cdot f(E(k), E_L)$ is then done where the function f is a function of the intrinsic energy E(k) of the x-ray pulse 16 and the intrinsic gain energy $E_L$.

$I_{coor,L,2}(j,k)$ provides the values of the pixels of the corrected radiographic image.

The finite correction function $f(E(k),E_L)$ is predetermined either experimentally, or through simulation calculations accounting for the geometry of the radiography equipment, the spectrum of the x-ray pulses 16 and the spectral sensitivity of the intermediate sensors 28 and the image sensors 8.

An example is described below of a method for determining the finite correction function f, in reference to FIGS. 4 to 6.

Reference signals $I_{BR}$ generated by the intermediate sensors 28 based on the angle θ from which they are seen, for a plurality of x-ray pulses 16 with different intrinsic energies E1, E2, E3, are simulated.

Figure 4:
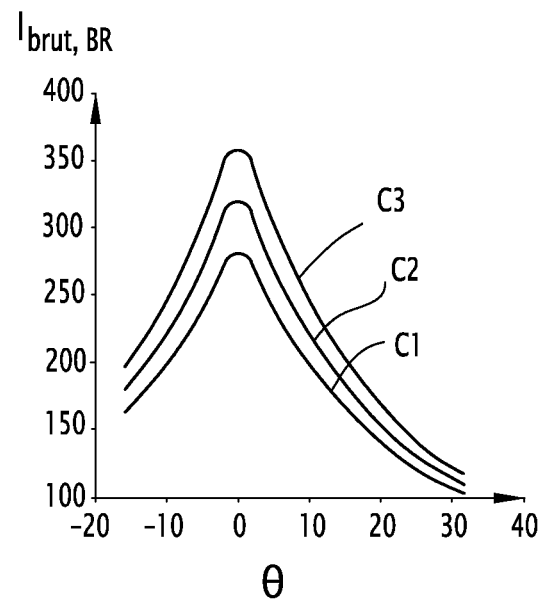
FIG. 4 is a graph showing a simulation, for three x-ray pulses with different intrinsic energies, of doses received by the intermediate sensors of the reference block of the equipment shown in FIG. 1 as a function of the angle corresponding to the sensors.
Figure 5:
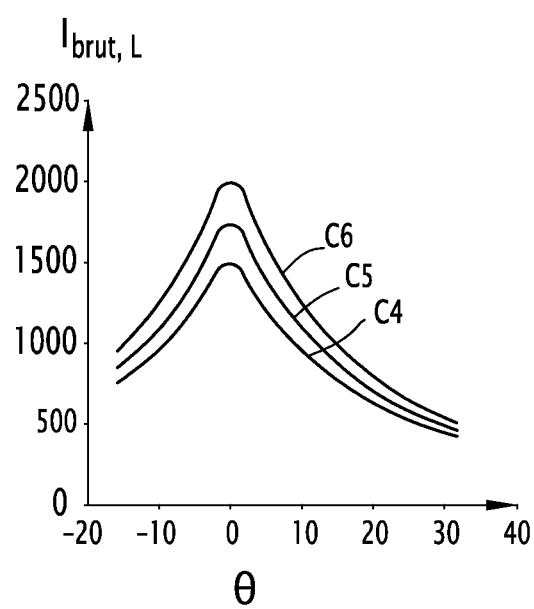
FIG. 5 is a graph showing a simulation of doses received by the receiving sensors as a function of the angle corresponding to those sensors.

Examples of simulated reference signals are illustrated in FIG. 4:
for curve C1, with an intrinsic energy E1 for example of 5.5 MeV,
for curve C2, with an intrinsic energy E2 for example of 6.0 MeV,
for curve C3, with an intrinsic energy E3 for example of 6.5 MeV.

Then, a simulation is done of raw image signals $I_L$ created by the receiving sensors 8 based on the angle θ from which they are seen, for the same x-ray pulses 16 with intrinsic energies E1, E2, E3, no load 11 being present in the intermediate space 36. FIG. 5 illustrates the obtained results:
for curve C4, at intrinsic energy E1,
for curve C5, at intrinsic energy E2,
for curve C6, at intrinsic energy E3.

The signals are normalized using signals obtained with the intrinsic energy E2, considered to be representative of the gain vector:

$$\begin{cases} I_{BR,1}(\theta) = \dfrac{I_{brut,BR}(\theta)}{(I_{brut,BR}(\theta))_{E=E2}} \\ I_{L,1}(\theta) = \dfrac{I_{brut,L}(\theta)}{(I_{brut,L}(\theta))_{E=E2}} \end{cases}$$

Next, the quotient $I_{coor,L}(\theta) = I_{brut,L,1}(\theta)/I_{BR,2}(\theta)$ is calculated. FIG. 6 illustrates the obtained results:
for curve C10, at intrinsic energy E1,
for curve C11, at intrinsic energy E2,
for curve C12, at intrinsic energy E3.

These curves have practically no θ dependence.

The function f is obtained from signals $I_{corr,L}(\theta)$.

It is advantageously obtained as the inverse of the mean of the signals $I_{corr,L}(\theta)$:

$f(E1,E2) = 1/\overline{I_{corr,L}(\theta)}$, $\overline{I_{corr,L}(\theta)}$ being the mean out of θ of the values $I_{corr,L}(\theta)$ obtained for an x-ray pulse with intrinsic energy E1, the signals $I_{brut,BR}(\theta)$ and $I_{brut,L}(\theta)$ having respectively been normalized by the signals $I_{brut,BR}(\theta)$ and $I_{brut,L}(\theta)$ obtained for an x-ray pulse with intrinsic energy E2, serving as gain vector.

Figure 6:
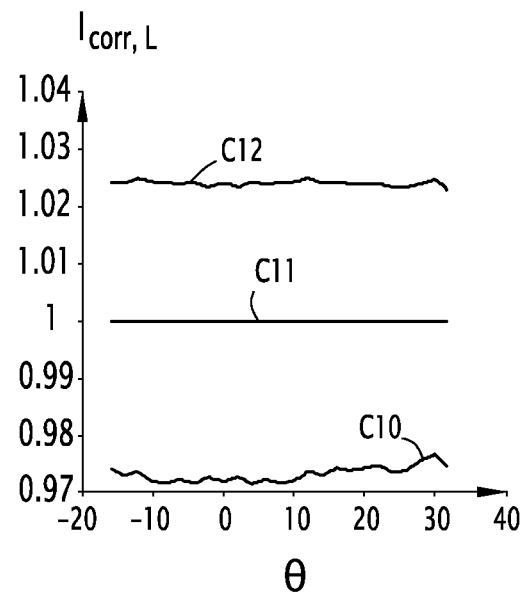
FIG. 6 is a graph showing the ratios obtained by dividing the doses received by the receiving sensors by those received by the intermediate sensors, the received doses having been normalized.

In the example of FIG. 6, the mean of curve C12 (θ) is approximately 1.025; the mean of curve C11 (θ) is approximately 1; the mean of curve C10 (θ) is approximately 0.975. This makes it possible to determine that:

$f(E1,E2) = 1/0.975$, $f(E2,E2) = 1$ $f(E3,E2) = 1/1.025$.

It will be understood that it is thus possible to determine the finite correction function f for any pair of intrinsic energy values.

The corrections successively applied to the raw image signals $I_{brut,L}(j,k)$ provide a corrected image $I_{coor,L,2}(j,k)$ that does not favor any angular direction θ, or any section k of the load 11.

According to a third embodiment of the radiography, called "interlaced", the source 2 for example emits x-ray pulses 16 with intrinsic energy 6.0 MeV at a rhythm of 200 Hz, alternating with x-ray pulses 16 with energy 4.0 MeV at a rhythm of 200 Hz. Two radiographic images are then obtained corresponding to two separate intrinsic energies E1 and E2.

Each image is next corrected in the manner described above in the second embodiment. For the first corrected image, the value of the pixel with coordinates (j,k) is given by $S1(j,k) = I_{coor,L,2}(j,k)$. For the second corrected image, the value of the pixel with coordinates (j,k) is given by $S2(j,k) = I_{coor,L,2}(j,k)$.

A single image, called "chemical discrimination", is then reconstituted from the two corrected images, which associates a value X(j,k) representative of the mean atomic number of materials of the load 11 passed through by the x-ray pulse 16 with rank k with each pixel with coordinates (j,k).

X(j,k) is then obtained using a function g, or "conversion table", that depends on the intrinsic energies of the x-ray pulses having generated the signals for the pixel in question:

$X(j,k) = g(S1(j,k), S2(j,k), E1(k), E2(k), j)$

A method for determining the function g is as follows. Two x-ray pulses with intrinsic energies E1 and E2 are simulated. The signals S1 and S2 are calculated after a test load consisting of a material MX with atomic number X and thickness e passes through. By varying X and e, curves S2=fX(j, E1, E2, S1) are established, where the function fX depends only on the material MX passed through. Knowing S1, S2 and j makes it possible to increase to X and therefore determines g(S1, S2, E1, E2, j).

Knowing the two intrinsic energies E1(k) and E2(k) for each pixel makes it possible to choose a conversion table suitable for the two actual intrinsic energies of the x-ray pulses having generated the signals and not reference values (in the example, 4.0 and 6.0 MeV).

Advantageously, it is possible to predetermine tables g for a set of discrete values of E1 and E2 covering the energy ranges in which E1(k) and E2(k) are located.

Without the reference block 6, this would not be possible; in that case, it would be necessary to settle for a frozen conversion table, predefined based solely on the reference values of the intrinsic energies and not on the actual intrinsic energies of the x-ray pulses 16.

In all of the embodiments of the invention, it is therefore possible to perform a more effective correction of the radiographic image $I_L(j,k)$, leading to an image with an improved quality $I_{coor,L}(j,k)$ or $I_{coor,L,2}(j,k)$. This is made possible using the "extended" reference block 6, i.e., comprising intermediate sensors 28 seen from separate angles in the median plane XOY.

Knowing the intrinsic energies not only improves the correction of the images, but also makes it possible to use an adapted conversion table, considerably closer to what is needed. The issue of the intrinsic energy of the x-ray pulses 16 not being stable is thus eliminated.

In one alternative, when the reference block 6 does not cover the entire angular opening ω of the incident beam 22, it is possible to perform interpolations and/or extrapolations to correct the image signals coming from the receiving sensors 8 corresponding to angular directions not covered by the reference block 6.

Consequently, it is advantageous, in order to limit the interpolations and/or extrapolations, to have a reference block 6 occupying at least 50%, preferably at least 90%, and if possible 100% of the angular opening ω of the incident beam.

Intermediate sensors 28 aligned, if possible regularly spaced, in a direction of the median plane XOY facilitate the correction operations.

When this alignment direction of the intermediate sensors 28 is perpendicular to the main direction OX' of the beam 22, the calculations are made easier, since they are generally symmetrical for the angle θ.

Scintillators 30 with a base of cesium iodide, cadmium tungstate or gadolinium oxysulfide yield good results, both for the receiving sensors 8 and the intermediate sensors 28.

The fact that the intermediate sensors 28 have scintillators 30 in the form of bars divided into physical pixels makes it possible to cover an angular sector continuously and to simplify the correction calculations.

Alternatively, the intermediate sensors 28 of the reference block 6 are distributed on a curved line (not shown), for example in an arc of circle, for example centered on the focal point F of the x-ray source 2.

In still another alternative, the reference block 6 includes at least two adjacent rows of intermediate reference sensors 28 capable of measuring fractions of the thickness e of the incident beam 22 in the direction OZ.

Figure 7:
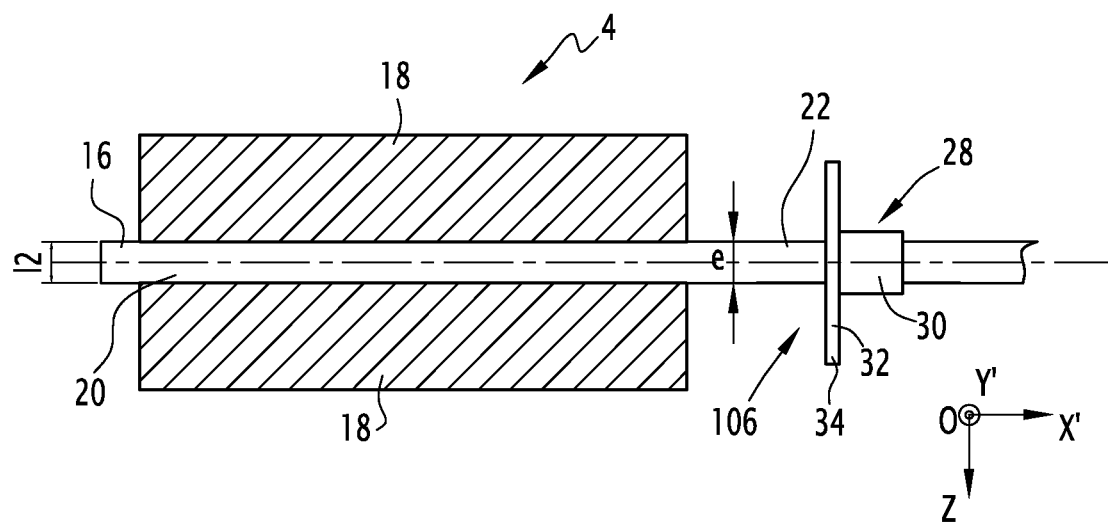
FIG. 7 shows an alternative of the device illustrated by FIG. 2.

FIG. 7 illustrates an alternative of the device shown in FIG. 2. The device shown in FIG. 8 is structurally similar to that shown in FIG. 2. It differs through the orientation of a reference block 106, which is deduced from that of the reference block 6 of FIG. 2 by a 90° clockwise rotation along the axis OY'. In the configuration shown in FIG. 8, the beam 22 therefore passes through the printed circuit 32 before passing through the scintillators 30.

In another alternative, the load 11 can be radiographed from angles other than that represented by the main direction OX' in FIG. 1, which illustrates a radiograph from the side. For example, the equipment 1 can be arranged to radiograph the load 11 from above, or from below, or from any other incidence. To that end, the relative position of the equipment 1 is modified with respect to the load 11, the operation of the equipment remaining the same.

The invention claimed is:

1. Equipment for the radiography of a load, the equipment and the load being designed to move relative to one another during the detection, the radiography equipment comprising:
    a source for emitting pulses of divergent X-rays;
    a collimator for the source for delimiting an incident X-ray beam designed to irradiate a section of the load, the successive X-ray pulses being capable of irradiating successive sections of the load; and
    sensors for receiving X-rays situated in the extension of the incident beam to receive the X-rays after they have passed through the load and generate raw image signals designed to be converted into a radiographic image portion corresponding to said section;
    wherein it further includes a reference block including intermediate X-ray sensors which are to be located each, at least partially, in the incident beam, between the source and the load, the intermediate sensors being designed to be irradiated by at least two separate angular sectors of the incident beam and to provide independent reference signals corresponding to each angular sector to be used in the conversion of the raw image signals into a portion of the radiographic image.

2. The radiography equipment according to claim 1, wherein the incident beam having a given angular opening in the median plane, the reference block comprises a plurality of intermediate sensors occupying, in the intermediate plane, an angular opening corresponding to at least 50% of said given angular opening.

3. The radiography equipment according to claim 1, wherein the intermediate sensors are substantially aligned, preferably regularly, in a direction R of the median plane.

4. The radiography equipment according to claim 3, wherein the direction R is substantially perpendicular to a main direction L of the incident beam in which the intensity of the incident beam is maximal.

5. The radiography equipment according to claim 1, wherein it includes a control and signal processing device capable of creating each radiographic portion by correcting each raw image signal collected in a given angular sector of the beam based on a reference signal obtained for the same given angular sector from the reference signals generated by the intermediate sensors for the same X-ray pulse.

6. The radiography equipment according to claim 1, wherein the intermediate sensors assume the form of bars.

7. The radiography equipment according to claim 1, wherein the intermediate sensors all have the same working detection volume.

8. A method for the radiography of a load, the method comprising the following steps:
    a) emitting a pulse of divergent X-rays from a source, the load and the source being in motion relative to one another;
    b) from the X-ray pulse, forming an incident X-ray beam using a collimator, and irradiating a section of the load extending along a median plane; and
    c) collecting the X-rays after they pass through the load in receiving sensors situated behind the load in the extension of the incident beam, and generating raw image signals corresponding to the X-ray doses received by the receiving sensors;
    steps a) and b) being iterated on successive sections of the load, said sections being defined by said motion and said pulse, so as to obtain a radiographic image of the load;
    the method further comprising a step d) in which a measurement is done of the X-ray doses received by at least two intermediate sensors of a reference block situated in the incident beam so as to be passed through by at least two separate angular sectors of the incident beam delimited in step b), generating independent reference signals corresponding to the doses measured by the intermediate sensors in each angular sector, and correcting the raw image signals obtained in step c) using reference signals.

9. The radiography method according to claim 8, wherein, in step d), the incident beam delimited in step b) having a given angular opening in the median plane, X-ray doses received by a plurality of intermediate sensors of the reference block situated in the incident beam so as to occupy an angular opening corresponding to at least 50% of said given annular opening are measured.

10. The radiography method according to claim 8, wherein, in step d), each raw image signal generated in step c) is corrected using a receiving sensor in a given angular sector of the beam through a calculation using a reference signal obtained for the same given angular sector from the reference signals generated by the intermediate sensors.

11. The radiography method according to claim 8, wherein, in step d), the reference signals created by the intermediate sensors are resampled in order to obtain the reference signals angularly corresponding with the raw image signals.

12. The radiography method according to claim 8, wherein, in step d), an intrinsic energy of the incident beam is evaluated from the reference signals and the raw image signals obtained in step c) are corrected through a calculation using said intrinsic energy.

13. The radiography method according to claim 12, wherein the evaluation of the intrinsic energy includes the following phases:

a measured angular distribution of the reference signals obtained for a given X-ray pulse from measured reference signals is established;

the measured angular distribution is compared with predetermined angular distributions corresponding to different intrinsic energies; and the measured angular distribution is associated with a predetermined angular distribution, and the intrinsic energy of the predetermined angular distribution is assigned to the given X-ray pulse.

14. The radiography method according to claim 12, wherein, in step d), an intrinsic gain energy of the reference block is further determined and said intrinsic energy of the reference block is taken into account in correcting the raw image signals obtained in step c).

15. The method according to claim 8, wherein, in step a), a first X-ray pulse is emitted at a first intrinsic reference energy, and a second X-ray pulse is next emitted at a second intrinsic reference energy separate from the first intrinsic reference energy, the method comprising the following steps:

determining the intrinsic energy corresponding to each x-ray pulse;

correcting the raw image signals respectively corresponding to each X-ray pulse using the intrinsic energy respectively determined for each x-ray pulse; and reconstituting a unique image from the corrected image signals, said unique image having information representative of the average atomic numbers of materials of the load.

16. The method according to claim 15, wherein the unique image is reconstituted, for each pixel, from the corrected image signals of said pixel and a conversion table depending on the intrinsic energies of the first and second X-ray pulses having generated the raw images of said pixel.

* * * * *